United States Patent [19]
Barley, Jr. et al.

[11] Patent Number: 5,653,769
[45] Date of Patent: Aug. 5, 1997

[54] METHODS FOR REDUCING SKIN IRRITATION FROM ARTIFICIAL DEVICES BY USE OF CYANOACRYLATE ADHESIVES

[75] Inventors: Leonard V. Barley, Jr., Colorado Springs; Patrick J. Tighe, Littleton, both of Colo.; Richard J. Greff, Yorba Linda, Calif.; Michael M. Byram, Colorado Springs, Colo.

[73] Assignee: MedLogic Global Corporation, Colorado Springs, Colo.

[21] Appl. No.: 542,034

[22] Filed: Oct. 12, 1995

Related U.S. Application Data

[63] Continuation of Ser. No. 200,953, Feb. 24, 1994, abandoned

[51] Int. Cl.$^6$ .......................... A61F 2/54; A61K 31/785; A61L 25/00
[52] U.S. Cl. .......................... 623/66; 623/33; 424/78.02; 424/400
[58] Field of Search .......................... 424/78.05, 78.02; 623/66, 33

[56] References Cited

U.S. PATENT DOCUMENTS

| | | |
|---|---|---|
| 2,804,073 | 8/1957 | Galliene et al. |
| 3,527,224 | 9/1970 | Rabinowitz |
| 3,591,676 | 7/1971 | Hawkins et al. |
| 3,667,472 | 6/1972 | Halpern |
| 3,699,076 | 10/1972 | Thomsen et al. ............... 424/78.02 |
| 3,995,641 | 12/1976 | Kronenthal et al. |
| 4,035,334 | 7/1977 | Davydov et al. |
| 4,287,177 | 9/1981 | Nakashima et al. |
| 4,444,933 | 4/1984 | Columbus et al. ............... 524/292 |
| 4,650,826 | 3/1987 | Waniczek et al. |
| 4,752,472 | 6/1988 | Kligman ............... 514/844 |
| 4,788,061 | 11/1988 | Shore ............... 424/448 |
| 4,958,748 | 9/1990 | Otake |
| 5,254,132 | 10/1993 | Barley et al. ............... 606/214 |
| 5,270,168 | 12/1993 | Grinnell |
| 5,306,490 | 4/1994 | Barley et al. |
| 5,403,591 | 4/1995 | Tighe et al. ............... 424/445 |
| 5,480,935 | 1/1996 | Greff et al. ............... 524/295 |
| 5,554,365 | 9/1996 | Byram et al. ............... 424/78.02 |
| 5,580,565 | 12/1996 | Tighe et al. ............... 424/400 |

OTHER PUBLICATIONS

Akers, et al., "Treating Friction Blisters with Alkyl–α–Cyanoacrylates", Arch. Dermatol., vol. 107, pp. 544–547, Apr. 1973.

Bhaskar,et al., "Healing of Skin Wounds with Butyl Cyanoacrylate", Journal of Dental Research, vol. 48, No. 2, pp. 294–297, 1969.

Dalvi, et al., "Non–suture Closure of Wound Using Cyanoacrylate", Journal of Postgraduate Medicine, vol. 32, No. 2, pp. 97–100, (1986).

Eiferman, et al., "Antibacterial Effects of Cyanoacrylate Glue", Archives of Ophthalmology, vol. 101, pp. 958–960, Jun. 1983.

Ellis, et al., "The Ideal Tissue Adhesive in Facial Plastic and Reconstructive Surgery", The Journal of Otolaryngology, vol. 19, No. 1, pp. 68–72, 1990.

Fung, et al., "Use of Butyl–2–Cyanoacrylate in Rabbit Auricular Cartilage", Archives of Otolaryngology, vol. 111, pp. 459–464, Jul. 1985.

Galil, et al., "The Healing of Hamster Skin Ulcers Treated with N–butyl–2–cyanoacrylate (Histoacryl blue)", pp. 601–607, 1984, Journal of Biomedical Materials Research, vol. 18, pp. 601–607, 1984.

Harper, "Stabilization of Osteochondral Fragments Using Limited Placement of Cyanoacrylate in Rabbits", Clinical Orthopaedics and Related Research, No. 231, pp. 272–276, Jun. 1988.

Kamer, et al., "Histoacryl: Its Use in Aesthetic Facial Plastic Surgery", Archives of Otolaryngology Head and Neck Surgery, vol. 115, pp. 193–197, Feb. 1989.

Kosko, "Upper Lid Blepharoplasty: Skin Closure Achieved with Butyl–2–Cyanoacrylate", Ophthalmic Surgery, vol. 12., pp. 424–425, Jun. 1981.

Lehman, et al., "Toxicity of Alkyl 2–Cyanoacrylate: Bacterial Growth", Archives of Surgery, vol. 93, pp. 447–450, Sep. 1966.

Leonard, et al., "Synthesis and Degradation of Poly(alkyl–α–Cyano–acrylate)", Journal of Applied Polymer Science, vol. 10, pp. 259–272, 1966.

Makady, et al., "Effect of tissue adhesives and suture patterns on experimentally induced teat lacerations in lactating dairy cattle", JAVMA, Reports of Original Studies, vol. 198, No. 11, pp. 1932–1934, Jun. 1991.

Matsumoto, "Bacteriology and Wound Healing", Chapter 3 in Tissue Adhesives in Surgery, pp. 106–113, 1972.

Matsumoto, "Clinical Considerations and Applications of Bucrylate Tissue Adhesive", Tissue Adhesives in Surgery, Chap. 1, Sec. III, pp. 226–237, 1972.

Matsumoto, "Reactions of the Organism to Acrylate–Adhesives", Tissue Adhesives in Surgery, pp. 436–444, 1972.

Matsumoto, et al., "Tissue Adhesive and Wound Healing", Archives of Surgery, vol. 98, pp. 266–271, Mar. 1969.

Mizrahi, et al., "Use of Tissue Adhesives in the Repair of Lacerations in Children", Journal of Pediatric Surgery, vol. 23, No. 4, pp. 312–313, Apr. 1988.

Morton, et al., "The Use of Histoacryl Tissue Adhesive for the Primary Closure of Scalp Wounds", Archives of Emergency Medicine, vol. 5, pp. 110–112, 1988.

Ousterhout, et al., "Cutaneous Absorption of n–Alkyl–α–Cyanoacrylate", Journal of Biomedical Materials Research, vol. 2, pp. 157–163, 1968.

Pepper, "Kinetics and Mechanism of Zwitterionic Polymerization of Alkyl Cyanoacrylate", Polymer Journal, vol. 12, No. 9., pp. 629–637, 1980.

(List continued on next page.)

Primary Examiner—Peter F. Kulkosky
Attorney, Agent, or Firm—Burns, Doane, Swecker & Mathis, L.L.P.

[57] ABSTRACT

A cyanoacrylate adhesive is applied onto surface skin areas prone to ulceration or irritation so as to inhibit irritation of the surface skin due to contact with an artificial device such as prosthetic devices, bandages, casts, etc.

15 Claims, No Drawings

OTHER PUBLICATIONS

Pepper, et al., "Kinetics of Polymerization of Alkyl Cyanoacrylate by Tertiary Amines and Phosphines", Makromol. Chem., vol. 184, pp. 395–410, 1983.

Ronis, et al., "Review of Cyanoacrylate Tissue Glues with Emphasis of Their Otorhinolaryngological Applications", Laryngoscope., vol. 94, pp. 210–213, Feb. 1984.

Saches, "Enbucrylate as Cartilage Adhesive in Augmentation Rhinoplasty", Archives of Otolaryngology, vol. 111, pp. 389–393, Jun. 1985.

Toriumi, et al., "Histotoxicity of Cyanoacrylate Tissue Adhesives: A Comparative Study", Archives of Otolaryngology Head and Neck Surgery, vol. 116, pp. 546–550, Jun. 1990.

Tseng, et al., "Modification of Synthesis and Investigation of Properties for 2–cyanoacrylate", Biomaterials, vol. 11, pp. 73–79, Jan. 1990.

Vinters, et al., "The Histotoxicity of Cyanoacrylate: A Selective Review", Neuroradiology, vol. 27, pp. 279–291, 1985.

Watson, "Use of Cyanoacrylate Tissue Adhesive for Closing Facial Lacerations in Children", British Medical Journal, vol. 299, p. 1014, Oct. 1989.

Chem. Abstract, CA079–027521 (05).

METHODS FOR REDUCING SKIN IRRITATION FROM ARTIFICIAL DEVICES BY USE OF CYANOACRYLATE ADHESIVES

This application is a continuation of application Ser. No. 08/200,953, filed Feb. 24, 1994, now abandoned.

BACKGROUND OF THE INVENTION

1. Field of the Invention

This invention is directed to methods for inhibiting surface skin irritation arising from friction between the skin surface and artificial devices such as tapes, prosthetic devices, casts, and the like by application of a layer of cyanoacrylate polymer to the skin area which is prone to such irritation. The cyanoacrylate adhesive to be used can be stored in dispensers for single or repeated/intermittent use and can be applied to the skin by spraying, painting, etc. of the adhesive.

2. State of the Art

Cyanoacrylate adhesives have been suggested for a variety of adhesive purposes including glues and surgical adhesives. In particular, cyanoacrylate adhesives of formula I:

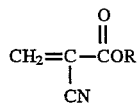
$$CH_2=C(CN)-COR \quad \quad I$$

wherein R is an alkyl or other suitable substituents are disclosed in U.S. Pat. Nos. 3,527,224; 3,591,676; 3,667,472; 3,995,641; 4,035,334; and 4,650,826. Typically, when used as adhesives for living tissues, the R substituent is alkyl of from 2 to 6 carbon atoms and most often is butyl (e.g., n-butyl).

The suggested medical uses for cyanoacrylate adhesives include surgical environments wherein the cyanoacrylate adhesives are utilized, e.g., as an alternative to sutures or as a hemostat.

In contrast to such prior art uses of cyanoacrylate adhesives, this invention is directed to methods for inhibiting surface skin irritation arising from friction between the skin surface and artificial devices in contact with the skin surface. Such artificial devices in contact with the skin surface are those devices which are attached or next to the human body and which can cause irritation to the skin surface (e.g., irritation due to friction arising from the constant or repeated rubbing of a device with the skin or irritation due to removal of tape from the skin surface due to the adhesive employed). Included within such artificial devices are prosthetic devices, casts, tapes, tubings, cannulae, bandages (e.g., BAND-AID® brand bandages), and the like.

With artificial devices such as prosthetic devices, casts and the like, once skin irritation arises it is difficult to treat primarily because such devices are not usually removed for the purpose of treating skin irritation unless the irritation becomes severe or results in an infection. With bandages, irritation due to the bandage adhesive and irritation and/or skin tears due to bandage removal causes discomfort and, in some cases, the individual may forego application of the bandage and the benefits ascribed thereto in order to prevent ensuing discomfort upon its removal. Accordingly, the health care industry has focused on measures to prevent the formation of skin irritation when such devices are used.

SUMMARY OF THE INVENTION

This invention is drawn to methods for inhibiting surface skin irritation arising from artificial devices attached or next to human skin by application of a layer of cyanoacrylate polymer to the skin area which is prone to such irritation. The layer of cyanoacrylate polymer is formed from application of cyanoacrylate adhesive to the skin surface and polymerization of the adhesive wherein application is typically, but not necessarily, conducted prior to development of skin irritation. The methods involve applying cyanoacrylate adhesive, particularly n-butyl cyanoacrylate adhesive, onto skin surface areas which will be in contact with the artificial device and which are prone to surface skin irritation so as to form a flexible, waterproof polymer layer over such skin areas. In turn, this polymer layer increases the skin integrity while reducing skin irritation to the underlying skin by forming a physical barrier layer interposed between the artificial device and the skin surface area.

Accordingly, in one of its method aspects, this invention is directed to a method for inhibiting irritation from an artificial device which contacts the human skin surface which method comprises:

applying to skin surface area(s) which will be in contact with the artificial device and which will be prone to surface skin irritation, a sufficient amount of a cyanoacrylate adhesive so as to cover said area(s);

polymerizing the cyanoacrylate adhesive so as to form a flexible, waterproof, adhesive polymer coating which adheres to the area(s) where the adhesive was applied; and attaching the artificial device such that at least a portion of the skin surface area(s) abutting said device has said adhesive polymer coating interposed between, wherein the cyanoacrylate, in monomeric form, is represented by formula I:

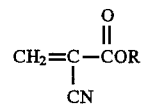
$$CH_2=C(CN)-COR \quad \quad I$$

where R is selected from the group consisting of:
alkyl of 2 to 10 carbon atoms,
alkenyl of 2 to 10 carbon atoms,
cycloalkyl groups of from 5 to 8 carbon atoms, phenyl,
2-ethoxyethyl,
3-methoxybutyl,
and a substituent of the formula:

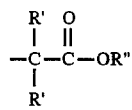
$$-C(R')(R')-C(=O)-OR''$$

wherein each R' is independently selected from the
group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably R is alkyl of from 2 to 10 carbon atoms and more preferably alkyl of from 2 to 8 carbon atoms. Even more preferably, R is butyl, pentyl or octyl and most preferably, R is n-butyl.

In a preferred embodiment, the cyanoacrylate is applied so as to provide from at least about 0.02 milliliter (ml), more preferably from about 0.02 to about 0.2 ml, and still more preferably from about 0.02 to about 0.1 ml, of cyanoacrylate adhesive per square centimeter of skin which is to be covered.

In another preferred embodiment, the cyanoacrylate adhesive to be applied to the skin has a viscosity of from 2 to about 1500 centipoise at 20° C. More preferably, the cyanoacrylate in the cyanoacrylate adhesive is almost entirely in monomeric form and the adhesive has a viscosity of from about 20 to about 100 centipoise at 20° C.

As used herein, the following terms have the following meanings:

The term "cyanoacrylate adhesive" refers to adhesive formulations comprising cyanoacrylate monomers of formula I:

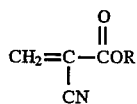

where R is selected from the group consisting of alkyl of 2 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

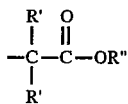

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate adhesive for use in the invention is n-butyl-2-cyanoacrylate.

The cyanoacrylate adhesives described herein rapidly polymerize in the presence of water vapor or tissue protein, and the n-butyl-cyanoacrylate is capable of bonding human skin tissue without causing histoxicity or cytotoxicity.

DETAILED DESCRIPTION OF THE PREFERRED EMBODIMENTS

This invention relates to cyanoacrylate adhesives which are useful for inhibiting surface skin irritation arising from artificial devices in contact with at least a portion of the human skin surface by application of a layer of cyanoacrylate polymer to that portion of the skin area prone to such irritation. The cyanoacrylate adhesive which is applied to surface skin areas prone to such irritation can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application, is not intended.

The cyanoacrylate adhesives used herein preferably have a viscosity of from 2 to about 1500 centipoise and more preferably from greater than 20 to about 100 centipoise at 20° C. It is contemplated, however, that pastes and gels having viscosities of up to 50,000 centipoise at 20° C. can also be employed and will make for easier skin application.

The specific viscosity of the formulation depends, in part, on the amount and degree of partially polymerized cyanoacrylate adhesive employed as well as additives which are employed in the formulation to enhance or decrease viscosity. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety. Additives which can be incorporated into the formulation to enhance its viscosity include polymers such as polymethyl methacrylate (PMMA) and polymerized cyanoacrylate adhesives as disclosed in U.S. Pat. Nos. 3,654,239 and 4,038,345 both of which are incorporated herein by reference in their entirety.

Monomeric forms of cyanoacrylate adhesives are often preferred where application is to be made to a large surface area. This preference results from the fact that those forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

For purposes of this invention, monomeric or partially polymerized n-butyl-2-cyanoacrylate is a particularly preferred adhesive and is capable of effectively bonding human skin tissue without causing histoxicity or cytotoxicity.

Upon contact with skin moisture and tissue protein, the cyanoacrylate adhesives will polymerize or, in the case of partially polymerized cyanoacrylate adhesives, will further polymerize, at ambient conditions (skin temperature) over about 10 to 60 seconds to provide a solid layer which forms over and strongly adheres to the surface of the skin. The resulting adhesive polymer layer or coating is flexible and waterproof thereby forming a protective layer which increases underlying skin integrity and reduces irritation to the surface skin area arising from the artificial device.

The surface skin areas prone to irritation due to contact with an artificial device are readily identified by conventional methods. The cyanoacrylate adhesive is applied to such irritation skin prone areas to provide an effectively thick coating over the human skin tissue. The cyanoacrylate adhesive forms a polymeric layer which provides an adhesive coating over the surface skin area prone to irritation which, when set, is waterproof and satisfactorily flexible and adherent to the tissue without premature peeling or cracking. Preferably, the adhesive coating has a thickness of less than about 0.5 millimeter (mm), and more preferably the coating has a thickness of less than about 0.3 mm. In a particularly preferred embodiment, the thickness of the adhesive coating is from about 0.1 millimeter to about 0.5 millimeter and even more preferably from about 0.1 millimeter to about 0.3 millimeter.

Adhesive coatings of such thicknesses form a physical barrier layer interposed between the artificial device and the human skin surface which coatings provide protection against artificial devices which cause surface skin irritation due to friction such as prosthetic devices and casts. Additionally, these coatings also provide protection against surface skin irritation due to the removal of artificial devices having an adhesive layer which maintains the location of the artificial device on the human skin surface. In the former case, irritation is reduced because the artificial device no longer contacts the skin surface and friction forces are either eliminated or reduced. In the latter case, irritation is reduced because the adhesive employed to maintain the location of the artificial device on the human skin surface no longer contacts the skin but rather contacts the polymeric coating. Moreover, since this coating naturally sloughs off the skin about 2–3 days after application, there is no need to effect removal of the coating from the skin surface. However, if early removal of this polymeric coating is desired, such can be achieved by use of solvents such as acetone.

The adhesive coating can be formed by applying at least about 0.02 ml of cyanoacrylate adhesive per square centimeter of skin, more preferably from about 0.02 to about 0.2 ml, and still more preferably from about 0.02 to about 0.1 ml, of cyanoacrylate adhesive per square centimeter of skin and yet more preferably from about 0.02 to about 0.05 ml of cyanoacrylate adhesive per square centimeter of skin.

FORMULATIONS

The cyanoacrylate adhesive formulations employed herein generally comprise monomeric and/or partially polymerized compounds of formula I described above and are sometimes referred to herein as simply cyanoacrylate adhesives. These formulations are liquid in nature and, upon contact with surface skin proteins and moisture, will polymerize to provide a solid film or layer over the skin surface.

The formulations may additionally contain one or more optional additives such as colorants, plasticizers, perfumes, anti-diffusion agents, modifying agents and stabilizers. In practice, each of these optional additives should be both miscible and compatible with the cyanoacrylate adhesive. Compatible additives are those that do not prevent the use of the cyanoacrylate adhesives in the manner described herein.

In general, colorants are added so that the polymerized film will contain a discrete and discernable color. Perfumes are added to provide a pleasant smell to the formulation. Stabilizers, such as sulfur dioxide, are added to minimize in situ polymerization in containers during storage. Plasticizers, such as dioctylphthalate or tri(p-cresyl) phosphate, are added in order to enhance the flexibility of the resulting polymer layer. Each of these additives is conventional. For example, suitable stabilizers are disclosed in U.S. Pat. No. 4,650,826 and suitable plasticizers are disclosed in U.S. Pat. Nos. 2,784,127 and 4,444,933 the disclosures of all of these patents being incorporated herein by reference in their entirety.

The amount of each of these optional additives employed in the cyanoacrylate adhesive is an amount necessary to achieve the desired effect.

The formulation is generally stored in an applicator for use in a single dose application or for use in repeated applications. Single dose applicators include those having breakable or removable seals that prevent moisture, including atmospheric moisture, from contacting the formulation and causing in situ polymerization.

For repeated and intermittent usage, minimal exposure to atmospheric moisture is required. This can be achieved by devices having very narrow outlets and low initial dead-space. One applicator for such repeated intermittent use is described in U.S. Pat. No. 4,958,748 which is incorporated herein by reference in its entirety.

Another applicator comprises a conventional spray applicator wherein the cyanoacrylate adhesive is sprayed onto the surface skin area prone to irritation due to friction with an artificial device. The spray rate of the applicator can be controlled so that application of a metered quantity of adhesive per unit area of skin surface over a set period of time is controlled.

Still another applicator comprises a brush or solid paddle applicator wherein the cyanoacrylate adhesive is "painted" onto the surface skin area prone to irritation due to friction with an artificial device.

A preferred applicator for repeated and intermittent usage is an applicator suitable for the non-sterile storage and metered dispersement of a cyanoacrylate adhesive after opening of the applicator wherein the applicator is characterized as having a resealable opening of no more than about 0.008 square inches (0.0516 square centimeters) so as to permit the metered dispersement of the adhesive from the applicator and which is capable of multiple administrations of the adhesive and is further characterized as having resealing means such as a cap which either tightly mates with the applicator or which screws onto the applicator.

Preferably, the opening of the applicator is about 0.0016 to about 0.003 square inches (about 0.0103 to about 0.0194 square centimeters).

In another preferred embodiment, the walls of the applicator are made of a pliable material, so that upon application of pressure onto the walls, the walls depress sufficiently to force the adhesive contained in the applicator through the opening. Preferably, the applicator is manufactured with its opening covered by a metal foil or other similar construction which closes this opening until the device is ready for use. The opening is then reinstated by use of a pin or similar device which punctures the covering.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions can be achieved without regard to the sterility of the formulation.

METHODOLOGY

The above-described formulations are applied to surface skin areas in contact with artificial devices attached to the human body which devices can cause irritation to the surface skin area(s) in contact therewith. Application is conducted under conditions suitable for polymerizing the adhesive so as to form a protective coating and can be conducted either prior to or after irritation develops. While preferably application is conducted prior to development of irritation, application after development of irritation will prevent further irritation and can enhance recovery of the irritated skin. In general, sufficient amounts of cyanoacrylate adhesive are employed to cover (i.e., coat) the entire surface skin area subjected to such irritation. The coating is preferably extended by at least about 1 centimeter and preferably by at least about 5 centimeters beyond the surface skin area prone to irritation.

The adhesive polymer coating should be maintained in a unbroken manner over the entire skin area prone to such surface skin irritation. This can be assured by careful application of the adhesive onto the skin. Additionally, the use of a plasticizer will facilitate the maintenance of the polymer coating in an unbroken manner. However, in a preferred embodiment, after the initial layer of adhesive has cured to provide for an adhesive polymer coating, a second, preferably thinner, layer is applied over the adhesive polymer coating. Additional amounts of cyanoacrylate adhesive can be applied as needed to maintain an unbroken coating covering over the irritation prone surface skin areas. For example, in the case of prosthetic devices, application of the cyanoacrylate adhesive to form the protective coating is typically made to the skin surface area which contacts the prosthetic device. In the case of bandages, application is made to that part of the skin surface where the adhesive of the bandage would otherwise contact the skin surface.

Sufficient cyanoacrylate adhesive is preferably employed to form a coating of from about 0.1 mm to less than about 0.5 mm thick. Such coatings can be formed by applying at least about 0.02 ml of cyanoacrylate adhesive per square centimeter of skin surface area.

The amount of cyanoacrylate adhesive applied onto the skin surface area can be controlled by the amount of adhesive packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive in a controlled dropwise manner. Other methods for the controlled dispersement of the cyanoacrylate adhesive are as described above including, by way of example, a conventional spray applicator, a brush or solid paddle applicator, and the like.

Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of an adhesive coating.

In general, the particular length of time required for polymerization will vary depending on factors such as the amount of adhesive applied, the temperature of the skin, the moisture content of the skin, the surface area of skin to which the adhesive was applied, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a coating while minimizing any action to prevent the adhesive from being dislodged from that portion of the skin where it was applied or to adhere to unintended objects. Excess adhesive polymer can be removed with acetone (nail polish remover) which can be readily conducted except in the case where the adhesive polymer binds to a sensitive skin part (e.g., the eye lids) where it should be removed by a health care professional.

After the adhesive coating has formed, the coating strongly adheres to the skin, is flexible and waterproof, thereby forming a protective coating which enhances the integrity of the underlying skin and protects the skin from further irritation thereby retarding or inhibiting surface skin irritation.

In general, the coating will adhere to the skin for a period of about 2–3 days after which time it sloughs off. Additional applications can be made if desired.

Because the cyanoacrylate polymer coating is waterproof, the patient is not prevented from bathing and other activities involving exposure to water during the period the adhesive layer protects this skin area.

The following examples illustrate certain embodiments of the invention but is not meant to limit the scope of the claims in any way.

EXAMPLES

Example 1

A cyanoacrylate adhesive formulation is prepared in monomeric form using n-butyl α-cyanoacrylate and which contains a colorant to readily ascertain where the formulation is applied, 20 weight percent of dioctyl phthalate which acts as a plasticizer to enhance the flexibility of the resulting polymer composition, and 200 parts per million (ppm) of sulfur dioxide which acts as a stabilizer.

The above described formulation is applied onto an approximately 80 square centimeter area of skin surface which will abut a prosthetic device, which in this case, is an artificial foot. The formulation is applied so as to provide 0.1 milliliter of adhesive per square centimeter of treated skin and, after application, the skin is maintained at ambient condition until a polymer coating forms in about 30 seconds. After the polymer coating has formed, the prosthetic device is attached.

The polymer coating strongly adheres to the skin surface and serves as a physical barrier integrated with the skin to protect the skin from friction and to improve adaption of the device to the body with decreased irritation.

Example 2

A cyanoacrylate adhesive formulation is prepared in monomeric form using n-butyl α-cyanoacrylate and which contains a colorant to readily ascertain where the formulation has been applied and 20 weight percent of dioctyl phthalate which acts as a plasticizer. The formulation is applied onto approximately 4 square centimeter areas corresponding to the adhesive areas of a bandage. The formulation is applied so as to provide about 0.1 milliliter of adhesive per square centimeter of treated skin and, after application, the skin is maintained at ambient condition until a polymer coating forms in about 30 seconds. After the polymer coating has formed, the bandage is applied in such a manner that the adhesive areas of the bandage overlay the polymer coatings. Insofar as the polymer coating forms a barrier layer between the adhesive areas of the bandage and the human skin surface, the bandage can be removed and optionally replaced without irritation to the underlying skin. Alternatively, the bandage can be maintained as applied until the polymer coating sloughs off after 2–3 days. At this point, the bandage also will fall off.

The method of this example inhibits skin irritation and/or allergic reaction due to bandage adhesive and inhibits skin tears when the bandage is removed. The polymer coating will naturally slough off from the skin over a period of about 2 to 3 days. This method increases comfort and improves skin integrity.

Example 3

A cyanoacrylate adhesive formulation is prepared in monomeric form using octyl α-cyanoacrylate which contains a colorant to readily ascertain where the formulation has been applied and about 200 ppm of sulfur dioxide which acts as a stabilizer.

The above described formulation is applied onto skin surface areas on the hand and upper arm which are to be in contact with the edges of a cast to be placed from the upper arm to the hand of a male patient in response to a broken wrist. The formulation is applied so as to provide about 0.1 milliliter of adhesive per square centimeter of treated skin and, after application, the skin is maintained at ambient condition until a polymer coating forms in about 30 seconds. After the polymer coating has formed, the cast is placed onto the arm.

In this example, the polymer coating prevents chaffing and skin irritation at the edges of the cast and is replaced as needed during the adaption period of the cast.

Also, the cyanoacrylate adhesive can be applied in the manner similar to Examples 1 and 3 after skin irritation due to attachment of a prosthesis or a cast respectively. Such irritated skin is characterized by redness and patient sensitivity.

From the foregoing description, various modifications and changes in the composition and method will occur to those skilled in the art. All such modifications coming within the scope of the appended claims are intended to be included therein.

What is claimed is:

1. A method for inhibiting irritation from prosthetic devices which contact the human skin surface which method comprises:

applying to unbroken skin surface area(s) without disorders which will be in contact with the prosthetic device and which will be prone to surface skin irritation, a sufficient amount of a cyanoacrylate adhesive so as to cover said area(s) and, which upon polymerization, forms a polymer layer on the skin surface having a thickness of less than about 0.5 mm;

polymerizing the cyanoacrylate adhesive so as to form a flexible, waterproof, adhesive polymer coating which adheres to the area(s) where the adhesive was applied; and subsequently directly placing the prosthetic device onto the skin surface such that at least a portion of said skin surface area(s) abutting said device has said polymer coating which adheres to the underlying skin and which forms a physical barrier interposed between the skin surface and the prosthetic device, wherein the cyanoacrylate, in monomeric form, is represented by formula I:

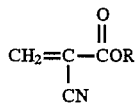

where R is selected from the group consisting of:
alkyl of 2 to 10 carbon atoms,
alkenyl of 2 to 10 carbon atoms,
cycloalkyl groups of from 5 to 8 carbon atoms,
phenyl,
2-ethoxyethyl,
3-methoxybutyl, and a substituent of the formula:

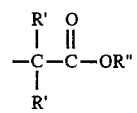

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

2. A method according to claim 1 wherein R is alkyl of from 2 to 8 carbon atoms.

3. A method according to claim 2 wherein R is butyl, pentyl or octyl.

4. A method according to claim 3 wherein R is n-butyl.

5. A method according to claim 1 wherein said adhesive is applied so as to provide at least 0.02 ml of cyanoacrylate adhesive per square centimeter of skin which is to be covered.

6. A method according to claim 5 wherein the cyanoacrylate adhesive is applied at a concentration of from about 0.02 ml to about 0.2 ml per square centimeter.

7. A method according to claim 6 wherein the cyanoacrylate adhesive is applied at a concentration of from about 0.02 ml to about 0.05 ml per square centimeter.

8. A method according to claim 1 wherein the cyanoacrylate adhesive has a viscosity of from 2 to about 1500 centipoise at 20° C.

9. A method according to claim 8 wherein the cyanoacrylate adhesive has a viscosity of from 20 to about 100 centipoise at 20° C.

10. A method according to claim 1 wherein the cyanoacrylate adhesive is applied from a single use applicator.

11. A method according to claim 1 wherein the cyanoacrylate adhesive is applied from a multiple, intermittent use applicator.

12. A method according to claim 1 wherein application of the cyanoacrylate adhesive to the skin surface prone to irritation is conducted prior to development of irritation.

13. A method according to claim 1 wherein application of the cyanoacrylate adhesive to the skin surface prone to irritation is conducted after development of irritation.

14. A method according to claim 1 wherein application of the cyanoacrylate adhesive to the skin surface prone to irritation is conducted in a manner such that the entire area of skin surface abutting the artificial device has said adhesive polymer coating interposed between.

15. A method for inhibiting irritation from prosthetic devices which contacts the human skin surface which method comprises:

applying to unirritated and unbroken skin surface areas without disorders which will be in contact with the prosthetic device and which will be prone to surface skin irritation, a sufficient amount of a cyanoacrylate adhesive so as to cover said area;

polymerizing the cyanoacrylate adhesive so as to form a flexible, waterproof, adhesive polymer coating which adheres to the area where the adhesive was applied wherein the thickness of the polymer coating on the skin surface is less than about 0.5 mm; and subsequently directly placing the prosthetic device onto the skin surface such that the entire area of the skin surface abutting said device has said polymer coating which adheres to the underlying skin and which forms a physical barrier interposed between the skin surface and the prosthetic device, wherein the cyanoacrylate, in monomeric form, is represented by formula:

$$CH_2=\underset{CN}{C}-\overset{O}{\overset{\|}{C}}OCH_2CH_2CH_2CH_3$$

* * * * *